(12) United States Patent
Muskett

(10) Patent No.: US 7,202,382 B2
(45) Date of Patent: Apr. 10, 2007

(54) PROCESS FOR THE PRODUCTION OF ACETIC ACID

(75) Inventor: Michael James Muskett, Hull (GB)

(73) Assignee: BP Chemicals Limited, Middlesex (GB)

( * ) Notice: Subject to any disclaimer, the term of this patent is extended or adjusted under 35 U.S.C. 154(b) by 370 days.

(21) Appl. No.: 10/509,831

(22) PCT Filed: Apr. 9, 2003

(86) PCT No.: PCT/GB03/01592

§ 371 (c)(1),
(2), (4) Date: Sep. 30, 2004

(87) PCT Pub. No.: WO03/097567

PCT Pub. Date: Nov. 27, 2003

(65) Prior Publication Data

US 2005/0165251 A1    Jul. 28, 2005

(30) Foreign Application Priority Data

May 20, 2002 (GB) .................. 0211560.8

(51) Int. Cl.
*C07C 51/12* (2006.01)
*C07C 51/14* (2006.01)
(52) U.S. Cl. ...................... 562/519; 562/522
(58) Field of Classification Search ............ None
See application file for complete search history.

(56) References Cited

U.S. PATENT DOCUMENTS

| | | | | |
|---|---|---|---|---|
| 5,237,097 A | | 8/1993 | Smith et al. ............. | 562/519 |
| 5,510,524 A | * | 4/1996 | Garland et al. ........... | 562/519 |
| 5,672,743 A | * | 9/1997 | Garland et al. ........... | 562/519 |
| 5,770,768 A | | 6/1998 | Denis et al. .............. | 562/519 |
| 5,877,348 A | * | 3/1999 | Ditzel et al. ............. | 562/519 |
| 5,942,460 A | * | 8/1999 | Garland et al. ........... | 502/150 |
| 6,472,558 B1 | * | 10/2002 | Key et al. ................ | 562/519 |

FOREIGN PATENT DOCUMENTS

| | | |
|---|---|---|
| EP | 0 846 674 A | 6/1998 |
| EP | 0 849 250 A | 6/1998 |
| FR | 2 795 410 A | 12/2000 |

* cited by examiner

Primary Examiner—Sikarl A. Witherspoon
(74) Attorney, Agent, or Firm—Nixon & Vanderhye

(57) ABSTRACT

A process for the production of acetic acid which comprises carbonylating methanol and/or a reactive derivative thereof in one or more reactors in a liquid reaction composition comprising iridium carbonylation catalyst, ruthenium promoter, methyl iodide co-catalyst, methyl acetate, acetic acid and water. The liquid reaction composition from the one or more reactors is passed to one or more flash separation stages to form (i) a vapor fraction comprising condensable components and a low pressure off-gas comprising carbon monoxide and (ii) a liquid fraction comprising iridium carbonylation catalyst, ruthenium promoter and acetic acid solvent. The condensable components are separated from the low pressure off-gas. The concentration of carbon monoxide in the low pressure off-gas is maintained according to the formula: $Y > mX + C$ wherein Y is the molar concentration of carbon monoxide in the low pressure off-gas, X is the concentration in ppm by weight of ruthenium in the liquid reaction composition, m is about 0.012 and C is about −8.7.

29 Claims, 2 Drawing Sheets

PROCESS FOR THE PRODUCTION OF ACETIC ACID

This application is the U.S. National Phase of International Application PCT/GB03/01592, filed 9 Apr. 2003, which designated the U.S.

The present invention relates to a process for the production of acetic acid by the carbonylation of methanol and in particular to a process for the production of acetic acid by the carbonylation of methanol in the presence of an iridium carbonylation catalyst and a ruthenium promoter.

The production of acetic acid by the carbonylation of methanol in the presence of an iridium catalyst and ruthenium promoter is described for example in U.S. Pat. No. 5,672,743, EP-A-0752406, EP-A-0849248, EP-A-0849249, EP-A-0849250, EP-A-0999198 and EP-A-1002785. In such liquid phase carbonylation processes, the acetic acid product may be recovered by withdrawing the liquid carbonylation composition from the carbonylation reactor subjecting the composition to one or more separation stages to recover the acetic acid product and returning other components of the composition to the carbonylation reactor.

The stability of the iridium carbonylation catalyst during the product recovery stage has been the subject of several patent applications such as for example WO 96/14286 and EP-A-0616997.

U.S. Pat. No. 5,237,097 relates to a carbonylation process in which the liquid carbonylation product solution is conveyed to a separation zone maintained at a lower total pressure than is the pressure in the reaction zone and simultaneously, there is introduced a carbon monoxide-containing gas contributing a partial pressure of up to 30 psia (0.21 MPa) of the total pressure in the separation zone. The Group VIII metal-containing catalyst is said to be preferably rhodium, ruthenium, palladium, cobalt and nickel, of which rhodium, cobalt and nickel are said to be particularly preferred and only rhodium is illustrated by example and is the subject of the claims.

EP-A-0728729 relates to a process for purifying a carboxylic acid fraction obtained by liquid phase carbonylation in which volatile iridium and/or volatile co-promoter (such as ruthenium, osmium and rhenium) contaminants are converted to involatile forms by contacting with an iodide in the absence of carbon monoxide or at a partial pressure of carbon monoxide less than that of the carbonylation reaction. It is stated therein that the partial pressure of carbon monoxide may be from 0 to 5 bar, preferably less than 0.25 bar. The issue of precipitation in the catalyst recycle loop is not considered.

It has been found that under certain operating conditions in an iridium-catalysed carbonylation process for the production of acetic acid, the catalyst system (that is the iridium catalyst and ruthenium promoter) may precipitate and form a solid. Typically, the solid is a mixture of catalyst and promoter and is usually red or reddish in colour. In particular, solid formation occurs when the liquid reaction composition is passed through a second reaction zone in which at least 1% of the dissolved and/or entrained carbon monoxide is reacted to produce additional acetic acid, such as described in EP-A-0846674.

Thus there remains a need for an improved carbonylation process in which promoter and/or catalyst losses due to the formation of solids during acetic acid product recovery are reduced.

It has now been found that by maintaining a defined amount of carbon monoxide during the acetic acid recovery stage and optional further reaction zone(s), the stability of the catalyst system may be improved and losses reduced.

Thus, according to the present invention there is provided a process for the production of acetic acid which process comprises the steps of (1) carbonylating methanol and/or a reactive derivative thereof in a first carbonylation reaction zone in a liquid reaction composition comprising iridium carbonylation catalyst, ruthenium promoter, methyl iodide co-catalyst, methyl acetate, acetic acid and water;

(2) withdrawing liquid reaction composition together with dissolved and/or entrained carbon monoxide and other gases from said carbonylation reaction zone;

(3) optionally passing said withdrawn liquid reaction composition through one or more further reaction zones to consume at least a portion of the dissolved and/or entrained carbon monoxide;

(4) passing said composition from step (2) and optional step (3) into one or more flash separation stages to form (i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and (ii) a liquid fraction comprising iridium carbonylation catalyst, ruthenium promoter and acetic acid solvent;

(5) separating the condensable components from the low pressure off-gas; and (6) recycling the liquid fraction from the flash separation stage to the first carbonylation reaction zone, wherein the concentration of carbon monoxide in the low pressure off-gas is maintained according to the formula:

$$Y > mX + C$$

wherein Y is the molar concentration of carbon monoxide in the low pressure off-gas, X is the concentration in ppm by weight of ruthenium in the liquid reaction composition, m is about 0.012 and C is about −8.7.

The process of the present invention solves the technical problem defined above by maintaining the amount of carbon monoxide in contact with the promoter above a defined level. This has been found to reduce the losses of promoter and/or catalyst due to instability during the acetic acid product recovery stages.

Without wishing to be bound by any theory, it is believed that the precipitation is, at least in part, due to the formation of polymeric forms of the ruthenium promoter in the flash separation zone.

It has been found that whilst a certain amount of instability can be tolerated since any precipitated solids can be re-dissolved on return to the carbonylation reactor, if the instability exceeds a certain level, the rate of dissolution is less than the rate of precipitation and there is a decrease in the amount of ruthenium promoter and iridium catalyst in the reactor. This requires the addition of more promoter and catalyst in order to maintain overall reactor activity.

The precipitated solid can itself present operational problems such as loss of material and blocking of process and/or instrument lines.

The first reaction zone may comprise a conventional liquid-phase carbonylation reaction zone. The pressure of the carbonylation reaction in the first reaction zone is suitably in the range 15 to 200 barg, preferably 15 to 100 barg, more preferably 15 to 50 barg and yet more preferably 18 to 35 barg. The temperature of the carbonylation reaction in the first reaction zone is suitably in the range 100 to 300° C., preferably in the range 150 to 220° C.

Preferably, two reaction zones are used, the first and second reaction zones being maintained in separate reaction vessels with means for withdrawing from the first reaction vessel and passing to the second reaction vessel liquid reaction composition from the first reaction vessel with dissolved and/or entrained carbon monoxide. Such a separate second reaction vessel may comprise a section of pipe between the first reaction vessel and a liquid reaction composition flashing valve. Preferably the pipe is liquid full. Typically the pipe's length to diameter ratio may be about 12:1, though length to diameter ratios both higher and lower than this may be employed.

Typically, at least a portion of the liquid reaction composition together with dissolved and/or entrained carbon monoxide is withdrawn from the first reaction zone and at least a portion of the withdrawn liquid and dissolved and/or entrained carbon monoxide passed to a second reaction zone. Preferably substantially all the liquid reaction composition together with dissolved and/or entrained carbon monoxide withdrawn from the first reaction zone is passed to the second reaction zone.

The second reaction zone may be operated at a reaction temperature in the range 100 to 300° C., preferably in the range 150 to 230° C. The second reaction zone may be operated at a temperature higher than the first reaction zone, typically up to 20° C. higher. The second reaction zone may be operated at a reaction pressure in the range 10 to 200 barg, preferably in the range 15 to 100 barg. Preferably, the reaction pressure in the second reaction zone is equal to or less than the reaction pressure in the first reaction zone. The residence time of liquid reaction composition in the second reaction zone is suitably in the range 5 to 300 seconds, preferably 10 to 100 seconds.

There may be introduced to the second reaction zone carbon monoxide in addition to that introduced to the second reaction zone as dissolved and/or entrained carbon monoxide. Such additional carbon monoxide may be co-joined with the first liquid reaction composition prior to introduction to the second reaction zone and/or may be fed separately to one or more locations within the second reaction zone. Such additional carbon monoxide may contain impurities, such as for example $H_2$, $N_2$, $CO_2$ and $CH_4$. The additional carbon monoxide may be comprised of high pressure off-gas from the first reaction zone which could advantageously allow the first reaction zone to be operated at a higher CO pressure with the resulting higher flow of carbon monoxide being fed to the second reaction zone. Additionally it could eliminate the requirement for a high pressure off-gas treatment.

The additional carbon monoxide may also be comprised of another carbon monoxide-containing gas stream such as for example a carbon monoxide-rich stream from another plant.

Preferably greater than 10%, more preferably greater than 25%, even more preferably greater than 50%, for example at least 95%, of the dissolved and/or entrained carbon monoxide in the withdrawn reaction composition from the first reaction zone is consumed in the second reaction zone.

In the process of the present invention, suitable reactive derivatives of methanol include methyl acetate, dimethyl ether and methyl iodide. A mixture of methanol and reactive derivatives thereof may be used as reactants in the process of the present invention. Water is required as co-reactant for ether or ester reactants. Preferably, methanol and/or methyl acetate are used as reactants.

At least some of the methanol and/or reactive derivative thereof will be converted to, and hence present as, methyl acetate in the liquid reaction composition by reaction with the carboxylic acid product or solvent. Preferably, the concentrations of methyl acetate in the liquid reaction compositions in the first and second reaction zones are independently in the range 1 to 70% by weight, more preferably 2 to 50% by weight, most preferably 3 to 35% by weight Water may be formed in situ in the liquid reaction compositions, for example, by the esterification reaction between methanol reactant and acetic acid product. Water may be introduced independently to the first and second carbonylation reaction zones together with or separately from other components of the liquid reaction compositions. Water may be separated from other components of reaction compositions withdrawn from the reaction zones and may be recycled in controlled amounts to maintain the required concentration of water in the liquid reaction compositions. Preferably, the concentrations of water in the liquid reaction compositions in the first and second reaction zones are independently in the range 0.1 to 20% by weight, more preferably 1 to 15% by weight, yet more preferably 1 to 10% by weight.

Preferably, the concentration of methyl iodide co-catalyst in the liquid carbonylation reaction compositions in the first and second reaction zones is independently in the range 1 to 20% by weight, preferably 2 to 16% by weight.

The iridium catalyst in the liquid reaction compositions in the first and second reaction zones may comprise any iridium-containing compound which is soluble in the liquid reaction compositions. The iridium catalyst may be added to the liquid reaction compositions in any suitable form which dissolves in the liquid reaction compositions or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction compositions of the first and second reaction zones is independently in the range 100 to 6000 ppm by weight of iridium.

The liquid reaction compositions in the first and second reaction zones additionally comprise at least one ruthenium promoter. The promoter may comprise any ruthenium-containing compound which is soluble in the liquid reaction compositions. The ruthenium promoter may be added to the liquid reaction compositions in any suitable form which dissolves in the liquid reaction compositions or is convertible to soluble form. Preferably, the ruthenium promoter compound may be used as chloride-free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, [Ru(CO)$_3$ I$_3$]$^-$H$^+$, tetra(aceto)chlororuthenium(II, III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cycloocta-1,5-diene)ruthenium (II) polymer and tris(acetylacetonate)ruthenium (III).

Preferably, the ruthenium-containing compounds are free of impurities which provide or generate in-situ ionic iodides which may inhibit the reaction, for example, alkali or alkaline earth metal or other metal salts.

Preferably, the ruthenium promoter is present in an effective amount up to the limit of its solubility in the liquid reaction compositions and/or any liquid process streams recycled to the carbonylation reaction zones from the acetic acid recovery stage. The ruthenium promoter is suitably present in the liquid reaction compositions at a molar ratio of each ruthenium promoter: iridium in the range [0.1 to 100]:1, preferably [greater than 0.5]:1, more preferably [greater than 1]:1 and preferably [up to 20]:1 more preferably [up to 15]:1 and yet more preferably [up to 10]:1.

The concentration of ruthenium promoter in the liquid reaction compositions in each of the first and second reaction zones is, independently, less than 6000 ppm. A suitable promoter concentration is 400 to 5000 ppm, such as 2000 to 4000 ppm.

Although in general it is preferred to operate the process in the substantial absence of added iodide salt, i.e. a salt generating or dissociating an iodide ion, it may be possible under certain conditions to tolerate such a salt. Accordingly, ionic contaminants such as, for example, (a) corrosion metals, particularly nickel, iron and chromium and (b) phosphines or nitrogen-containing compounds or ligands which may quaternise in situ, should be kept to a minimum or eliminated in the liquid reaction composition as these may generally have an adverse effect on the reaction by generating I$^-$ in the liquid reaction composition which has an adverse effect on the reaction rate. Some corrosion metal contaminants such as for example molybdenum have been found to be less susceptible to the generation of I$^-$. Corrosion metals which have an adverse effect on the reaction rate may be minimised by using suitable corrosion resistant materials of construction. Similarly, contaminants such as alkali metal iodides, for example lithium iodide, should be kept to a minimum. Corrosion metal and other ionic impurities may be reduced by the use of a suitable ion exchange resin bed to treat the reaction composition, or preferably a catalyst recycle stream. Such a process is described in U.S. Pat. No. 4,007,130. Preferably, ionic contaminants are kept below a concentration at which they would generate less than 500 ppm I$^-$, preferably less than 250 ppm I$^-$ in the liquid reaction composition, more preferably less than 50 ppm I$^-$.

The carbon monoxide reactant for the carbonylation reactions may be essentially pure or may contain inert impurities such as carbon dioxide, methane, nitrogen, noble gases, water and C$_1$ to C$_4$ paraffinic hydrocarbons. The presence of hydrogen in the carbon monoxide and generated in situ by the water gas shift reaction is preferably kept low, for example, less than 1 bar partial pressure, as its presence may result in the formation of hydrogenation products. The partial pressure of carbon monoxide in the first and second reaction zones is suitably independently in the range 1 to 70 bar, preferably 1 to 35 bar and more preferably 1 to 15 bar.

Acetic acid product may be recovered from the second reaction zone and optionally together with or separately from the first reaction zone by flash separation. In flash separation liquid reaction composition is passed to a flashing zone via a flashing valve. The flash separation zone may be an adiabatic flash vessel or may have additional heating means. In the flash separation zone a liquid fraction comprising the majority of the iridium catalyst and the majority of the ruthenium promoter is separated from a vapour fraction comprising acetic acid, carbonylatable reactant, water and methyl iodide carbonylation co-catalyst and non-condensable gases such as nitrogen, carbon monoxide, hydrogen and carbon dioxide; the liquid fraction being recycled to the first reaction zone and the vapour fraction being passed to one or more distillation zones. In a first distillation zone acetic acid product is separated from the light components (methyl iodide and methyl acetate). The light components are removed overhead, and recycled to the first and/or second reaction zones. Also removed overhead is a low pressure off-gas comprising the non-condensable gases such as nitrogen, carbon monoxide, hydrogen and carbon dioxide. Such a low-pressure off-gas stream may be passed through an off-gas treatment section to remove condensable materials such as methyl iodide, prior to being vented to atmosphere, for example, via a flare.

In accordance with the present invention, the concentration of carbon monoxide in the low pressure off-gas must be greater than a concentration defined by the concentration of ruthenium according to the formula $Y > mX + C$.

Suitably, the concentration of carbon monoxide in the low pressure off gas is at least 30 mol %, such as 30 to 60 mol %, for example, 30–40 mol % and the ruthenium concentration in the liquid reaction composition is up to 3000 ppm by weight.

Preferably, the concentration of carbon monoxide in the low pressure off gas is at least 50 mol %, preferably in the range 50 to 60 mol. % and the ruthenium concentration in the liquid reaction composition is up to 6000 ppm by weight.

More preferably, the concentration of carbon monoxide in the low pressure off gas is at least 55 mol %, such as in the range 55 to 65 mol. % and the ruthenium concentration in the liquid reaction composition is up to 5500 ppm by weight.

The acetic acid produced by the process according to the present invention may be further purified by conventional processes, for example further distillation to remove impurities such as water, unreacted carbonylation reactant and/or ester derivative thereof and higher-boiling by-products.

The process of the present invention is preferably performed as a continuous process.

BRIEF DESCRIPTION OF THE DRAWINGS

The present invention will now be illustrated by way of example only and with reference to the following Examples and FIGS. 1 and 2.

EXPERIMENT A AND
EXAMPLES/EXPERIMENTS 1–18

Figure 1:
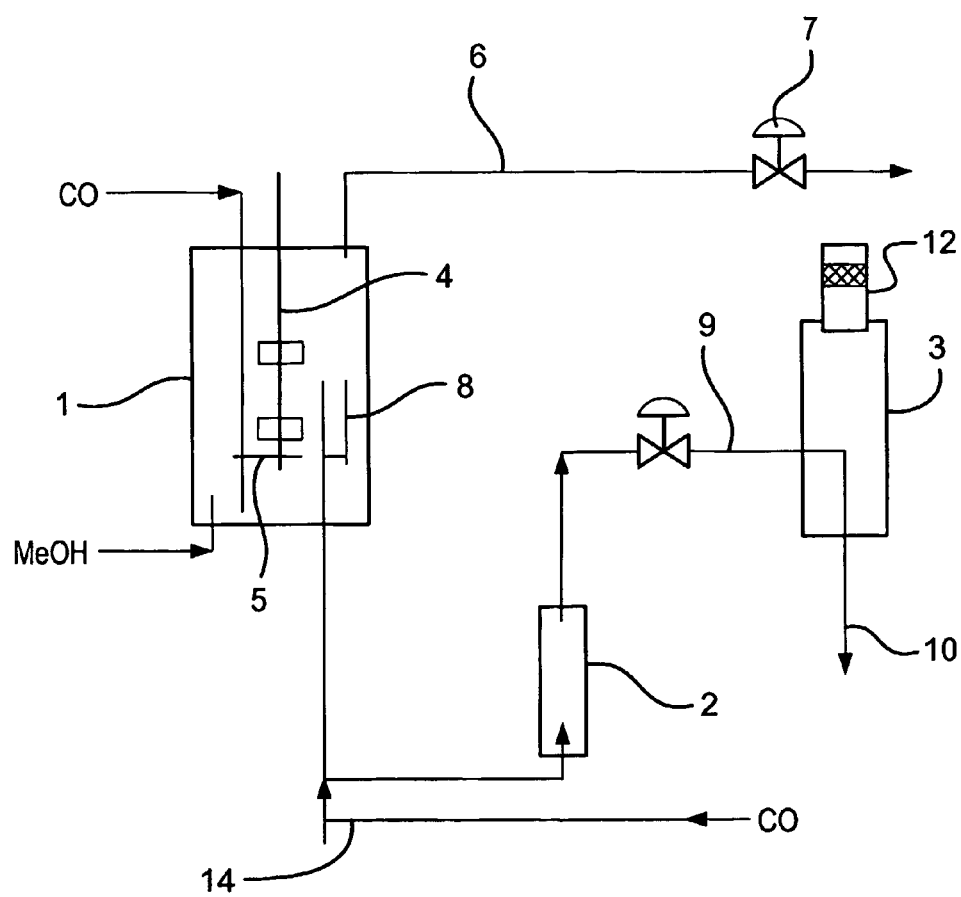
FIG. 1 is a schematic diagram of the apparatus used in the Examples.

The apparatus used is shown in FIG. 1. With reference to FIG. 1 the apparatus comprised a stirred primary carbonylation reactor (1), a secondary carbonylation reactor (2), a flash tank (3) and a distillation column (not shown).

Commercial grade methanol, which has been used to scrub the off-gas was carbonylated in the 6 liter primary reactor (1) in the presence of an iridium carbonylation catalyst and a ruthenium promoter at a pressure of 27.6 barg ($2.76 \times 10^6$ N/m$^2$) and a temperature of 190° C. The primary reactor (1) was fitted with a stirrer/propeller (4) and a baffle cage (not shown) to ensure intimate mixing of the liquid and gaseous reactants. Carbon monoxide was supplied from pressure bottles, to the primary reactor (1) via a sparge (5) fitted beneath the stirrer (4). To minimise iron ingress into the primary reactor (1) the carbon monoxide was passed through a carbon filter (not shown). A jacket (not shown), through which the hot oil is circulated, enabled the reaction liquid in the primary reactor (1) to be maintained at a constant reaction temperature. As a measure of the rate of solids formation, the rate of fouling on a near infra-red cell located on the reactor sample loop was used. This was operated at 90° C. and was located on the reactor outlet (flashing line) immediately up-stream of the flashing valve. The fouling was measured as absorption units/day.

To purge inerts, high pressure off-gas was removed from the primary reactor (1) through line (6). It was passed through a condenser (not shown) before the pressure was dropped across valve (7) and prior to being fed into the scrubbing system. Liquid reaction composition was withdrawn from the primary reactor (1) down a still well (8) via line (9) into the flash tank (3) under reactor level control. In the flash tank (3) the liquid reaction composition was flashed down to a pressure of 1.48 barg ($1.48 \times 10^5$ N/m$^2$). The resulting mixture of vapour and liquid was separated; the catalyst-rich liquid was returned to the primary reactor (1) by line (10) and pump (not shown) and the vapour was passed through a demister (12) and then directly into the distillation column (not shown) as vapour.

A secondary reactor (2) volume was attached to the flashing line (9) and fitted with isolation valves such that the flow exiting the primary reactor (1) either passed directly to the flashing valve or directly through the secondary reactor (2) to the flashing valve. The secondary reactor (2) comprised a pipe of diameter 2.5 cm, length 30 cm and together with associated pipework had a volume of either approximately 4% or 8% of the primary reactor (1). The pipe was placed in parallel to the flashing line (9), and was provided with a supply of additional carbon monoxide via line 14. The secondary reactor (2) was operated at the same pressure as the primary reactor (1).

The vapour from the demister (12) entered the distillation column (not shown) where aqueous acetic acid was recovered from the vapour through a side draw-off (not shown) of the distillation column (not shown) and was further purified and dried in a purification system (not-shown) and a low pressure off-gas comprising carbon monoxide was passed to a scrubber (not shown) before being flared.

Experiment A

Using the apparatus and method as described with reference to FIG. 1 and wherein the flow exiting the primary reactor (1) passes directly to the flashing valve (that is no secondary reactor was employed) methanol was carbonylated in the primary reactor (1) at 190° C. and a total pressure of 27.6 barg ($2.76 \times 10^6$ N/m$^2$). A liquid reaction composition was withdrawn from the primary reactor (1) through line (9). The liquid reaction composition in the primary reactor (1) comprised approximately 7% by weight of methyl iodide, approximately 10% by weight of methyl acetate, approximately 4% by weight of water, approximately 79% by weight of acetic acid, 1450 ppm of iridium and 4450 ppm ruthenium. The liquid reaction composition from the primary reactor (1) was passed to the flash separation vessel (3) operated at a pressure of 1.48 barg ($1.48 \times 10^5$ N/m$^2$). The rate of fouling was measured using near infra-red analysis as described above and the results are shown in Table 2.

EXAMPLE 1

Using the apparatus and method described with reference to FIG. 1, methanol was carbonylated in the primary reactor (1) at 190° C. and a total pressure of 27.6 barg ($2.76 \times 10^6$ N/m$^2$). A liquid reaction composition was withdrawn from the primary reactor (1) through line (9). The liquid reaction composition in the primary reactor (1) comprised approximately 7% by weight of methyl iodide, 11% by weight of methyl acetate, 4% by weight of water, approx. 78% by weight of acetic acid, 1520 ppm of iridium and 4410 ppm ruthenium. Then, the liquid reaction composition withdrawn from the primary reactor (1) was diverted into the second reactor (2). The liquid reaction composition was further carbonylated in the second reactor (2) at a mid temperature of 190° C. and a total pressure of 27.6 barg ($2.76 \times 10^6$ N/m$^2$) with a residence time of 40–50 seconds.

The liquid reaction composition from the second reactor (2) was passed to the flash separation vessel (3) operated at a pressure of 1.48 barg ($1.48 \times 10^5$ N/m$^2$). The rate of fouling was measured using near infra-red analysis as described above and the results are shown in Table 2.

EXAMPLES 2 to 4

The process of Example 1 was repeated with the operating conditions as shown in Table 1. The concentrations of ruthenium and carbon monoxide in the low pressure off-gas were varied as shown in Table 2.

EXPERIMENTS 5 to 18

The process of Example 1 was repeated with the operating conditions as shown in Table 1 except that either the concentration of ruthenium was greater than 6000 ppm or the concentration of carbon monoxide in the low pressure off-gas was less than 50 mol %. The concentrations of ruthenium and carbon monoxide in the low pressure off-gas are shown in Table 2.

TABLE 1

|  | [H20] wt % | [MeI] wt % | [MeOAc] wt % | [Ir] ppm | [Ru] ppm | 2$^{nd}$ reactor CO feed g/h | 2$^{nd}$ reactor volume % |
|---|---|---|---|---|---|---|---|
| Experiment A | 4.4 | 6.5 | 9.6 | 1450 | 4450 | — | — |
| Example 1 | 4.3 | 6.9 | 11.2 | 1460 | 4330 | 200 | 8 |
| Example 2 | 4.1 | 6.1 | 7.7 | 1460 | 4300 | 200 | 8 |
| Example 3 | 4.2 | 7.0 | 10.1 | 1440 | 3370 | 200 | 8 |

TABLE 1-continued

|  | [H2O] wt % | [MeI] wt % | [MeOAc] wt % | [Ir] ppm | [Ru] ppm | 2nd reactor CO feed g/h | 2nd reactor volume % |
|---|---|---|---|---|---|---|---|
| Example 4 | 4.1 | 7.0 | 10.6 | 1530 | 4920 | 100 | 4 |
| Experiment 5 | 4.1 | 7.3 | 10.6 | 1520 | 4410 | — | 8 |
| Experiment 6 | 3.8 | 6.2 | 8.8 | 1390 | 4220 | 130 | 8 |
| Experiment 7 | 4.5 | 7.6 | 10.6 | 1400 | 4270 | 120 | 8 |
| Experiment 8 | 4.2 | 6.7 | 11.0 | 1460 | 3230 | 140 | 8 |
| Experiment 9 | 4.2 | 6.7 | 10.4 | 1460 | 3220 | 90 | 8 |
| Experiment 10 | 4.4 | 6.8 | 10.6 | 1450 | 3210 | 50 | 8 |
| Experiment 11 | 4.4 | 6.8 | 10.8 | 1420 | 2980 | 10 | 8 |
| Experiment 12 | 4.4 | 6.5 | 10.1 | 1490 | 6210 | 200 | 8 |
| Experiment 13 | 3.8 | 6.5 | 9.7 | 1480 | 6110 | 150 | 8 |
| Experiment 14 | 3.9 | 6.7 | 10.5 | 1420 | 5750 | 100 | 8 |
| Experiment 15 | 3.8 | 6.5 | 10.2 | 1510 | 4830 | 10 | 4 |
| Experiment 16 | 5.1 | 6.9 | 12.6 | 1830 | 2430 | 0 | 8 |
| Experiment 17 | 4.6 | 7.5 | 13.5 | 1970 | 2490 | 0 | 8 |
| Experiment 18 | 4.6 | 6.9 | 9.7 | 1550 | 2880 | 0 | 8 |

TABLE 2

|  | [Ru] ppm | Carbonylation rate mol/l/h | ppCO bara | LP off-gas [CO] mol % | Rate of fouling AU/day | 2nd reactor Exit Temp ° C. |
|---|---|---|---|---|---|---|
| Experiment A | 4450 | 22.0 | 8.3 | 48 | 0.01 | — |
| Example 1 | 4430 | 24.2 | 7.8 | 56 | 0.01 | 192.7 |
| Example 2 | 4300 | 23.6 | 9.5 | 63 | 0.01 | 194.0 |
| Example 3 | 3370 | 26.2 | 11.5 | 57 | 0.01 | 195.9 |
| Example 4 | 4920 | 27.2 | 11.8 | 57 | 0.00 | 188.5 |
| Experiment 5 | 4410 | 25.2 | 8.2 | 32 | 0.11 |  |
| Experiment 6 | 4220 | 23.9 | 8.2 | 45 | 0.11 | 193.5 |
| Experiment 7 | 4270 | 28.9 | 9.7 | 45 | 0.20 | 195.4 |
| Experiment 8 | 3230 | 26.8 | 11.2 | 42 | 0.06 | 196.3 |
| Experiment 9 | 3220 | 24.9 | 10.7 | 31 | 0.08 | 195.7 |
| Experiment 10 | 3210 | 24.4 | 10.2 | 23 | 0.06 | 194.6 |
| Experiment 11 | 2980 | 23.5 | 9.9 | 13 | 0.15 | 193.0 |
| Experiment 12 | 6210 | 28.9 | 9.8 | 55 | 0.02 | 196.0 |
| Experiment 13 | 6110 | 30.1 | 10.1 | 47 | 0.22 | 196.2 |
| Experiment 14 | 5750 | 29.2 | 10.3 | 39 | 0.42 | 195.6 |
| Experiment 15 | 4830 | 27.4 | 11.7 | 42 | 0.02 | 189.3 |
| Experiment 16 | 2430 | 25.3 | 9.7 | 18 | 0.05 |  |
| Experiment 17 | 2490 | 24.6 | 6.2 | 7 | 0.30 |  |
| Experiment 18 | 2880 | 17.7 | 8.1 | 10 | 0.08 |  |

From the results of Examples 1–4 and Experiments 5–18 it can be seen that when the concentration of ruthenium promoter is less than 6000 ppm and the concentration of carbon monoxide in the low-pressure off-gas is at least 50 mol %, there is virtually no precipitation (fouling). In addition it can be seen that the degree of precipitation is in line with precipitation occurring in the absence of a secondary reactor. When the concentrations of ruthenium promoter and carbon monoxide in the low-pressure off-gas fall outside these ranges, the rate of precipitation (fouling) of solids is significant.

EXAMPLES 19 to 22, EXPERIMENTS 23

The process of Example 1 was repeated with the operating conditions as shown in Table 3. The concentrations of ruthenium and carbon monoxide in the low pressure off-gas were varied as shown in Table 4.

TABLE 3

|  | [H2O] wt % | [MeI] wt % | [MeOAc] wt % | [Ir] ppm | [Ru] ppm | 2nd reactor CO feed g/h | 2nd reactor volume % |
|---|---|---|---|---|---|---|---|
| Example 19 | 5.3 | 7.0 | 12.9 | 1370 | 4160 | — | — |
| Example 20 | 4.9 | 6.2 | 12.5 | 1750 | 3980 | 0 | 4 |
| Example 21 | 5.0 | 6.9 | 12.8 | 1270 | 3790 | 0 | 4 |
| Example 22 | 4.8 | 6.7 | 13.0 | 1180 | 3490 | — | — |
| Experiment 23 | 5.0 | 6.8 | 12.6 | 1750 | 3850 | 0 | 4 |

TABLE 4

|  | [Ru] ppm | Carbonylation rate mol/l/h | ppCO bara | LP off-gas [CO] mol % | Rate of fouling AU/day |
|---|---|---|---|---|---|
| Example 19 | 4160 | 20.2 | 9.3 | 60 | 0.000 |
| Example 20 | 3980 | 22.3 | 9.4 | 37 | −0.001 |
| Example 21 | 3790 | 19.9 | 9.9 | 44 | 0.003 |
| Example 22 | 3490 | 18.8 | 9.4 | 59 | −0.001 |
| Experiment 23 | 3850 | 22.1 | 9.0 | 30 | −0.001 |

EXAMPLES 24 to 26 and
EXPERIMENTS 27 to 34

The process of Example 1 was repeated with the operating conditions as shown in Table 5. The concentrations of ruthenium and carbon monoxide in the low pressure off-gas were varied as shown in Table 6. The rate of fouling was determined by the accumulation of solid on a filter placed in the catalyst recycle line.

TABLE 5

|  | [H2O] wt % | [MeI] wt % | [MeOAc] wt % | [Ir] ppm | [Ru] ppm | $2^{nd}$ reactor CO feed g/h | $2^{nd}$ reactor volume % |
|---|---|---|---|---|---|---|---|
| Example 24 | 4.9 | 6.8 | 12.1 | 1530 | 3440 | 90 | 8 |
| Example 25 | 4.7 | 5.9 | 12.2 | 1390 | 3220 | 80 | 8 |
| Example 26 | 5.2 | 6.7 | 11.7 | 1580 | 3370 | 40 | 8 |
| Experiment 27 | 4.8 | 7.2 | 11.2 | 1670 | 3650 | 60 | 8 |
| Experiment 28 | 5.0 | 7.1 | 11.9 | 1570 | 3380 | 20 | 8 |
| Experiment 29 | 5.2 | 6.6 | 11.9 | 1570 | 3380 | 0 | 8 |
| Experiment 30 | 4.4 | 6.5 | 11.5 | 1650 | 4360 | 60 | 8 |
| Experiment 31 | 4.9 | 6.1 | 11.8 | 1680 | 5130 | 60 | 8 |
| Experiment 32 | 4.8 | 6.7 | 12.3 | 1480 | 4910 | 60 | 8 |
| Experiment 33 | 5.0 | 6.9 | 11.8 | 1410 | 5780 | 60 | 8 |
| Experiment 34 | 4.3 | 6.2 | 9.8 | 1590 | 6260 | 60 | 8 |

TABLE 6

|  | [Ru] ppm | Carbonylation rate mol/l/h | ppCO bara | LP off-gas [CO] mol % | Rate of fouling g/h |
|---|---|---|---|---|---|
| Example 24 | 3440 | 22.1 | 9.5 | 57 | 0.0038 |
| Example 25 | 3220 | 21.3 | 9.3 | 52 | 0.0034 |
| Example 26 | 3370 | 21.0 | 9.8 | 35 | 0.0037 |
| Experiment 27 | 3650 | 21.5 | 9.3 | 45 | 0.0088 |
| Experiment 28 | 3380 | 20.9 | 9.6 | 27 | 0.0043 |
| Experiment 29 | 3380 | 20.2 | 9.9 | 12 | 0.0063 |
| Experiment 30 | 4360 | 21.5 | 9.2 | 43 | 0.0112 |
| Experiment 31 | 5130 | 22.6 | 9.9 | 42 | 0.0123 |
| Experiment 32 | 4910 | 22.6 | 8.2 | 43 | 0.0116 |
| Experiment 33 | 5780 | 21.9 | 9.0 | 40 | 0.0090 |
| Experiment 34 | 6260 | 23.9 | 9.9 | 41 | 0.0143 |

From a comparison of the results of Examples 24 to 26 with Experiments 27 to 34 in Table 6 it can clearly be seen that where the concentration of carbon monoxide in the low pressure off-gas is maintained according to the formula:

$$Y > mX + C$$

wherein Y is the molar concentration of carbon monoxide in the low pressure off-gas, X is the concentration in ppm by weight of ruthenium in the liquid reaction composition, m is about 0.012 and C is about −8.7 the rate of fouling is significantly reduced.

Figure 2:
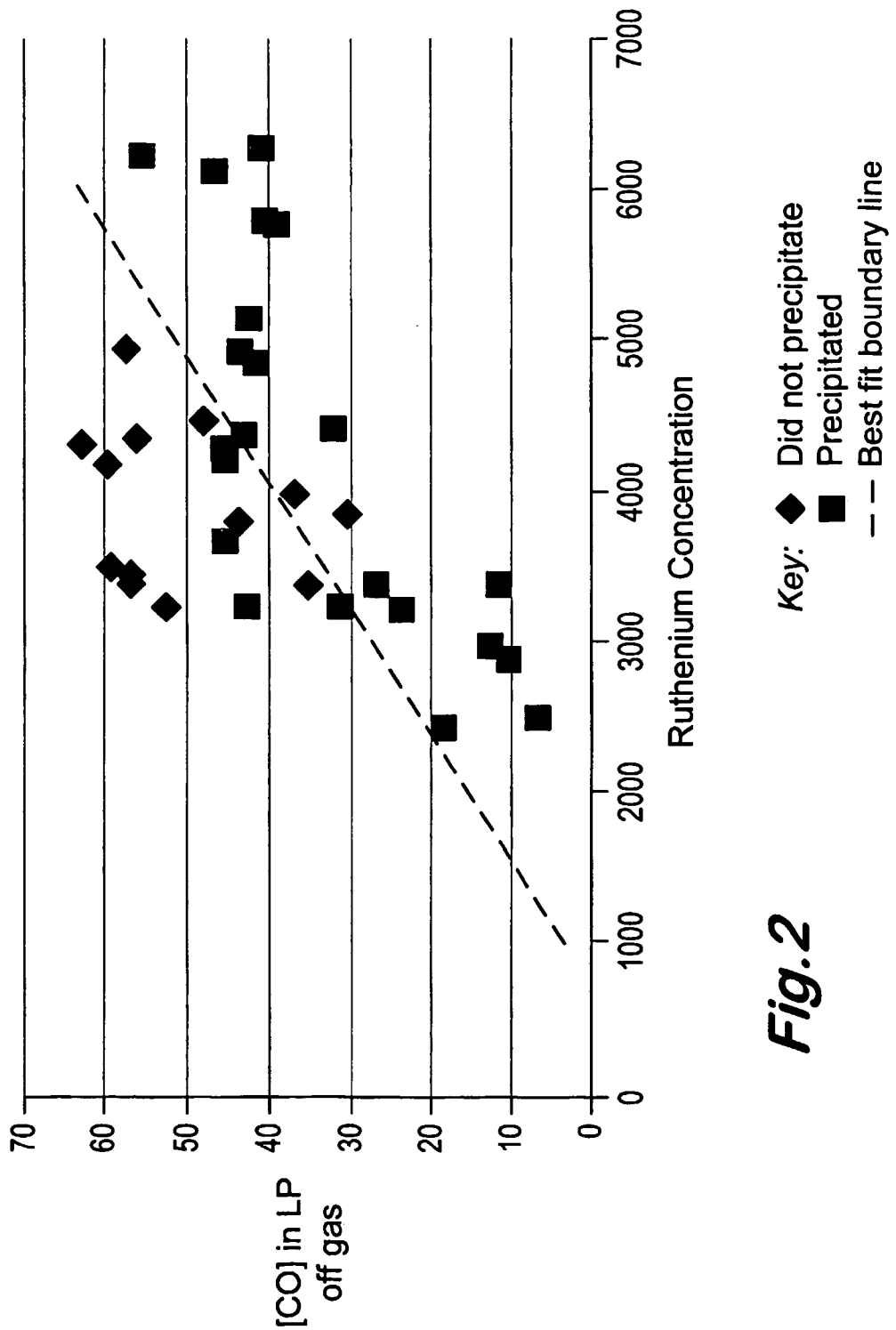
FIG. 2 is a graph of the effects of carbon monoxide and ruthenium concentration on solids precipitation.

FIG. 2 illustrates in a graph the relationship between carbon monoxide concentration in the low pressure off-gas and the ruthenium concentration and the formation of solids. The data points in the graph are the results of the Examples and Experiments in Tables 1 to 6 above. From the graph a correlation was developed (dotted line) which indicates that solids formation is mitigated if the carbon monoxide concentration Y in the low pressure off-gas is maintained according to the formula:

$$Y > mX + C$$

wherein Y is the molar concentration of carbon monoxide in the low pressure off-gas, X is the concentration in ppm by weight of ruthenium in the liquid reaction composition, m is about 0.012 and C is about −8.7. Where the fouling rate is greater then 0.01 AU/day or 0.004 g/h it has been assumed that solids formation occurs.

The invention claimed is:

1. A process for the production of acetic acid which process comprises the steps of (1) carbonylating methanol and/or a reactive derivative thereof in a first carbonylation reaction zone in a liquid reaction composition comprising iridium carbonylation catalyst, ruthenium promoter, methyl iodide co-catalyst, methyl acetate, acetic acid and water;

(2) withdrawing liquid reaction composition together with dissolved and/or entrained carbon monoxide and other gases from said carbonylation reaction zone;

(3) optionally passing said withdrawn liquid reaction composition through one or more further reaction zones to consume at least a portion of the dissolved and/or entrained carbon monoxide;

(4) passing said composition from step (2) and optional step (3) into one or more flash separation stages to form (i) a vapour fraction comprising condensable components and low pressure off-gas, the condensable components comprising acetic acid product and the low pressure off-gas comprising carbon monoxide and other gases dissolved and/or entrained with the withdrawn liquid carbonylation reaction composition and (ii) a liquid fraction comprising iridium carbonylation catalyst, ruthenium promoter and acetic acid solvent:

(5) separating the condensable components from the low pressure off-gas; and (6) recycling the liquid fraction from the flash separation stage to the first carbonylation reaction zone, wherein the concentration of carbon monoxide in the low pressure off-gas is maintained according to the formula:

$$Y > mX + C$$

wherein Y is the molar concentration of carbon monoxide in the low pressure off-gas, X is the concentration in ppm by weight of ruthenium in the liquid reaction composition, m is about 0.012 and C is about −8.7.

2. A process according to claim 1 wherein the liquid reaction composition together with dissolved and/or entrained carbon monoxide withdrawn from the first reaction zone is passed through a second reaction zone.

3. A process according to claim 2 wherein substantially all the liquid reaction composition together with dissolved and/or entrained carbon monoxide withdrawn from the first reaction zone is passed to the second reaction zone.

4. A process according to claim 2 wherein carbon monoxide in addition to that introduced to the second reaction zone as dissolved and/or entrained carbon monoxide is introduced into the second reaction zone.

5. A process according to claim 4 wherein the additional carbon monoxide is co-joined with the first liquid reaction composition prior to introduction to the second reaction zone and/or is fed separately to one or more locations within the second reaction zone.

6. A process according to claim 4 wherein the additional carbon monoxide contains impurities.

7. A process according to claim 4 wherein the additional carbon monoxide comprises high pressure off-gas from the first reaction zone.

8. A process according to claim 4 wherein the additional carbon monoxide comprises a carbon monoxide-containing gas stream.

9. A process according to claim 2 wherein greater than 10% of the dissolved and/or entrained carbon monoxide in the liquid reaction composition withdrawn from the first reaction zone is consumed in the second reaction zone.

10. A process according to claim 2 wherein greater than 25% of the dissolved and/or entrained carbon monoxide in the liquid reaction composition withdrawn from the first reaction zone is consumed in the second reaction zone.

11. A process according to claim 2 wherein greater than 50% of the dissolved and/or entrained carbon monoxide in the liquid reaction composition withdrawn from the first reaction zone is consumed in the second reaction zone.

12. A process according to claim 1 wherein methanol and/or methyl acetate are carbonylated with carbon monoxide in the first reaction zone.

13. A process according to claim 1 wherein the concentration of methyl acetate in the liquid reaction compositions in the first and second reaction zones are independently in the range 1 to 70% by weight.

14. A process according to claim 1 wherein the concentration of water in the liquid reaction compositions in the first and second reaction zones are independently in the range 0.1 to 20% by weight.

15. A process according to claim 1 wherein the concentration of methyl iodide co-catalyst in the liquid reaction compositions in the first and second reaction zones is independently 1 to 20% by weight.

16. A process according to claim 1 wherein the concentration of iridium carbonylation catalyst in the liquid reaction compositions in the first and second reaction zones is independently in the range 100 to 6000 ppm.

17. A process according to claim 1 wherein the ruthenium promoter is present in the liquid reaction compositions in the first and second reaction zones at a molar ratio of each ruthenium promoter: iridium in the range [0.1 to 100]:1.

18. A process according to claim 1 wherein the ruthenium promoter is present in the liquid reaction compositions in the first and second reaction zones at a molar ratio of each ruthenium promoter: iridium in the range [up to 10]:1.

19. A process according to claim 1 wherein the concentration of ruthenium in the liquid reaction compositions in the first and second reaction zones is independently less than 6000 ppm.

20. A process according to claim 1 wherein the concentration of ruthenium in the liquid reaction compositions in the first and second reaction zones is independently 400 to 5000 ppm.

21. A process according to claim 1 wherein the partial pressure of carbon monoxide in the first and second reaction zones is independently in the range 1 to 70 bar.

22. A process according to claim 1 wherein the partial pressure of carbon monoxide in the first and second reaction zones is independently in the range 1 to 15 bar.

23. A process according to claim 1 wherein the concentration of carbon monoxide in the low pressure off-gas is at least 30 mol % and the concentration of ruthenium in the liquid reaction composition is up to 3000 ppm by weight.

24. A process according to claim 23 wherein the concentration of carbon monoxide in the low pressure off-gas is 30 to 40 mol % and the concentration of ruthenium in the liquid reaction composition is up to 3000 ppm by weight.

25. A process according to claim 1 the concentration of carbon monoxide in the low pressure off-gas is at least 50 mol % and the concentration of ruthenium in the liquid reaction composition is up to 6000 ppm by weight.

26. A process according to claim 25 wherein the concentration of carbon monoxide in the low pressure off-gas is 50 to 60 mol % and the concentration of ruthenium in the liquid reaction composition is up to 6000 ppm by weight.

27. A process according to claim 1 wherein the concentration of carbon monoxide in the low pressure off gas is at least 55 mol % and the ruthenium concentration in the liquid reaction composition is up to 5500 ppm by weight.

28. A process according to claim 27 wherein the concentration of carbon monoxide in the low pressure off gas is in the range 55 to 65 mol. % and the ruthenium concentration in the liquid reaction composition is up to 5500 ppm by weight.

29. A process according to claim 1 wherein the process is operated as a continuous process.

* * * * *